(12) United States Patent
Eguchi et al.

(10) Patent No.: US 10,246,393 B2
(45) Date of Patent: Apr. 2, 2019

(54) METHOD FOR PRODUCING AROMATIC COMPOUND

(71) Applicants: TOSOH CORPORATION, Yamaguchi-ken (JP); KYOTO UNIVERSITY, Kyoto (JP)

(72) Inventors: Hisao Eguchi, Yamaguchi-ken (JP); Takanori Miyazaki, Yamaguchi-ken (JP); Yoshiaki Nakao, Kyoto (JP)

(73) Assignees: TOSOH CORPORATION, Yamaguchi-Ken (JP); KYOTO UNIVERSITY, Kyoto (JP)

(*) Notice: Subject to any disclaimer, the term of this patent is extended or adjusted under 35 U.S.C. 154(b) by 0 days.

(21) Appl. No.: 15/797,568

(22) Filed: Oct. 30, 2017

(65) Prior Publication Data
US 2018/0118646 A1    May 3, 2018

(30) Foreign Application Priority Data

Oct. 31, 2016 (JP) ................................. 2016-213752

(51) Int. Cl.
| | |
|---|---|
| C07D 213/06 | (2006.01) |
| C07C 41/30 | (2006.01) |
| C07C 1/32 | (2006.01) |
| C07C 17/263 | (2006.01) |
| C07C 45/61 | (2006.01) |
| C07C 67/28 | (2006.01) |
| C07C 303/30 | (2006.01) |
| C07D 213/16 | (2006.01) |
| C07D 213/64 | (2006.01) |
| C07D 215/06 | (2006.01) |
| C07D 217/04 | (2006.01) |
| C07D 295/033 | (2006.01) |
| C07D 409/04 | (2006.01) |
| C07C 67/343 | (2006.01) |
| C07C 41/18 | (2006.01) |
| C07B 37/04 | (2006.01) |
| C07C 315/04 | (2006.01) |
| C07C 45/45 | (2006.01) |
| C07C 45/49 | (2006.01) |
| C07C 45/59 | (2006.01) |

(52) U.S. Cl.
CPC .............. *C07C 41/30* (2013.01); *C07B 37/04* (2013.01); *C07C 1/321* (2013.01); *C07C 1/323* (2013.01); *C07C 17/263* (2013.01); *C07C 41/18* (2013.01); *C07C 45/45* (2013.01); *C07C 45/49* (2013.01); *C07C 45/59* (2013.01); *C07C 45/61* (2013.01); *C07C 67/28* (2013.01); *C07C 67/343* (2013.01); *C07C 303/30* (2013.01); *C07C 315/04* (2013.01); *C07D 213/16* (2013.01); *C07D 213/64* (2013.01); *C07D 215/06* (2013.01); *C07D 217/04* (2013.01); *C07D 295/033* (2013.01); *C07D 409/04* (2013.01); *C07C 2527/12* (2013.01); *C07C 2603/24* (2017.05)

(58) Field of Classification Search
CPC .. C07D 213/06; C07D 215/02; C07D 217/02; C07D 409/04
USPC ........................ 544/106; 546/134, 152, 280.4
See application file for complete search history.

(56) References Cited

U.S. PATENT DOCUMENTS

| | | | |
|---|---|---|---|
| 5,550,236 A * | 8/1996 | Schlosser ................ | C07B 37/04 544/224 |
| 5,618,975 A | 4/1997 | Wagner et al. | |
| 5,633,400 A | 5/1997 | Wagner et al. | |
| 5,756,804 A | 5/1998 | Haber et al. | |
| 6,140,265 A | 10/2000 | Haber et al. | |
| 6,399,779 B1 | 6/2002 | Marcuccio et al. | |
| 6,417,357 B1 | 7/2002 | Tinkl et al. | |
| 6,559,310 B2 | 5/2003 | Marcuccio et al. | |
| 6,693,210 B2 | 2/2004 | Miyaura | |
| 6,946,560 B2 * | 9/2005 | Buchwald ................. | C07C 1/26 546/339 |

(Continued)

FOREIGN PATENT DOCUMENTS

| | | |
|---|---|---|
| JP | 2005-60335 | 3/2005 |
| JP | 2008-63260 | 3/2008 |

(Continued)

OTHER PUBLICATIONS

Parvinder Pal Singh et al., "Iron-catalyzed Cross-Coupling of Electron-Deficient Heterocyles and Quinone with Organoboron Species via Innate C—H Functionalization: Application in Total Synthesis of Pyrazine Alkaloid Botryllazine A"; The Journal of Organic Chemistry, 78 (6); 2013; pp. 2639-2648.

(Continued)

*Primary Examiner* — Jeffrey H Murray
(74) *Attorney, Agent, or Firm* — Greenblum & Bernstein, P.L.C.

(57) ABSTRACT

In a cross coupling reaction, in a case where a halogen atom is selected as the leaving group of the raw material compound, a harmful halogen waste forms as a by-product after the reaction, and disposal of the waste liquid is complicated and environmental burden is high. In a carbon-hydrogen activation cross coupling reaction which requires no halogen atom as the leaving group, although no halogen waste forms as a by-product, the reaction substrate is considerably restricted, and the reaction remains a limited molecular construction method.

A method for producing an aromatic compound, which comprises subjecting an aromatic nitro compound and a boronic acid compound to a cross coupling reaction in the presence of a metal catalyst.

3 Claims, No Drawings

(56) References Cited

U.S. PATENT DOCUMENTS

| | | |
|---|---|---|
| 7,411,082 B2 | 8/2008 | Ley et al. |
| 2001/0020104 A1 | 9/2001 | Haber et al. |
| 2009/0143586 A1 | 6/2009 | Scherer et al. |

FOREIGN PATENT DOCUMENTS

| | | |
|---|---|---|
| JP | 2008-184418 | 8/2008 |
| JP | 2013-60426 | 4/2013 |
| WO | 2005/096784 | 10/2005 |
| WO | 2015/148931 | 10/2015 |

OTHER PUBLICATIONS

Akira Suzuki, "Recent Developments of Biaryl Synthesis via Cross-coupling Reactions of Areneboronic Acid Derivatives"; Journal of Synthetic Organic Chemistry, 63 (4); 2005; pp. 312-324.

Xingwang Zheng et al., "The Coupling of Arylboronic Acids with Nitroarenes Catalyzed by Rhodium"; Organic Letters, 13 (7); 2011; pp. 1726-1729.

Sushilkumar S. Bahekar et al., "CuI catalyzed C—S bond formation by using nitroarenes"; Catalysis Communications, 41; 2013; pp. 123-125.

Hisao Eguchi et al., "Development and Industrialization of Efficient Cross-Coupling Reactions", Journal of Synthetic Organic Chemistry; 70 (9); 2012; pp. 937-946.

M. Ramu Yadav et al., "The Suzuki-Miyaura Coupling o fNitroarenes"; Journal of American Chemical Society, 139; 2017; pp. 9423-9426.

Journal of the American Chemical Society, 127(33), 11763-11768, 2005.

Extended European Search Report in respect to European Application No. 17198805.8, dated Mar. 29, 2018.

Mondal et al., "O-Arylation with nitroarenes: metal-catalyzed and metal free methodologies", New Journal of Chemistry, vol. 39, No. 1, Jan. 1, 2015, pp, 31-37.

Zhang et al., Ligand-free copper-catalyzed coupling of nitroarenes with arylboronic acids, Green Chemistry, vol. 14, No. 4, Jan. 1, 2012, pp. 912-916.

Qin et al., "Suzuki-Miyaura Cross-Coupling of Arenediazonium Salts with Arylboronic Acids Catalyzed by Recyclable Polymer-Supported N-Heterocyclic Carbene-Palladium Catalyst", Synlett, vol. 2007, No. 15, Sep. 1, 2007, pp. 2410-2414.

\* cited by examiner

METHOD FOR PRODUCING AROMATIC COMPOUND

TECHNICAL FIELD

The present invention relates to a method for producing an aromatic compound. More specifically, it relates to a method for producing an aromatic compound, which comprises conducting a cross coupling reaction using an aromatic nitro compound and a boronic acid compound as raw materials.

BACKGROUND OF INVENTION

A multisubstituted aromatic compound is widely used in a pharmaceutical and agrochemical field, a natural product synthesis field, a liquid crystal and organic electroluminescence field, etc., and as a method for constructing its molecular skeleton, various means have been developed. Among them, a reaction for synthesizing a linked aromatic compound using an aromatic boronic acid derivative (Suzuki cross coupling reaction) is one of particularly useful means, and various modifications have been conducted (Non-Patent Document 1).

As the raw material of Suzuki cross coupling reaction, an aromatic compound having a leaving group is commonly used. As the leaving group, a halogen atom such as a chlorine atom, a bromine atom or an iodine atom is most often used. Further, in recent years, a method of conducting a cross coupling reaction (carbon-hydrogen activation) directly from an aromatic compound having no leaving group such as a halogen atom has been proposed (Non-Patent Document 2).

PRIOR ART DOCUMENTS

Non-Patent Documents

Non-Patent Document 1: Akira Suzuki, Journal of Synthetic Organic Chemistry, Japan, 2005, 63, 312
Non-Patent Document 2: Journal of Organic Chemistry, 78 (6), 2639-2648; 2013

SUMMARY OF INVENTION

Technical Problem

In a case where a halogen atom is selected as the leaving group, a harmful halogen waste forms as a by-product after the reaction, and disposal of the waste liquid is complicated and environmental burden is heavy. In a carbon-hydrogen activation cross coupling reaction which requires no halogen atom as the leaving group, although no halogen waste forms as a by-product, the reaction substrate is considerably restricted, and the reaction remains a limited molecular construction method.

Solution to Problem

The present inventors have found, as a means to produce a desired aromatic compound without forming a halogen waste as a by-product, a method for producing an aromatic compound, which comprises subjecting an aromatic nitro compound and a boronic acid compound to a cross coupling reaction in the presence of a metal catalyst.

Advantageous Effects of Invention

According to the present invention, it is possible to provide an industrially excellent production method by which no harmful halogen waste forms as a by-product and thus the environmental burden is reduced. Further, the reaction substrate can be freely and widely selected as compared with conventional technology, and a desired aromatic compound can be produced industrially efficiently. Further, a high purity aromatic compound can be obtained by a simple purification operation such as column chromatography, distillation or recrystallization from the obtained aromatic compound. Further, as the case requires, the aromatic compound may be converted to another compound via several steps. A cross coupling reaction in which the leaving group is a nitro group is unprecedented, and a non-conventional molecular skeleton construction process can be proposed by employing the method of the present invention.

DETAILED DESCRIPTION OF INVENTION

Now, the present invention will be described in further detail.

The present invention provides a method for producing an aromatic compound, which comprises subjecting an aromatic nitro compound and a boronic acid compound to a cross coupling reaction in the presence of a metal catalyst.

The aromatic nitro compound is not particularly limited and may, for example, be a nitrated aromatic hydrocarbon compound or a nitrated heteroaromatic compound. The aromatic nitro compound is not particularly limited and may be represented by the following formula (1):

$$Ar^1-(-NO_2)_n \qquad (1)$$

wherein $Ar^1$ is an aromatic hydrocarbon group which may have a substituent or a heteroaromatic group which may have a substituent, and n is an integer of from 1 to 5.

The aromatic hydrocarbon group which may have a substituent is not particularly limited and may, for example, be a phenyl group which may have a substituent, a biphenyl group which may have a substituent, a naphthyl group which may have a substituent, an anthracenyl group which may have a substituent, a pyrenyl group which may have a substituent, a terphenyl group which may have a substituent, a phenanthracenyl group which may have a substituent, a perylenyl group which may have a substituent or a triphenylenyl group which may have a substituent.

The heteroaromatic group which may have a substituent is not particularly limited and may, for example, be a furanyl group which may have a substituent, a benzofuranyl group which may have a substituent, a dibenzofuranyl group which may have a substituent, a phenyldibenzofuranyl group which may have a substituent, a dibenzofuranylphenyl group which may have a substituent, a thienylenyl group which may have a substituent, a benzothienyl group which may have a substituent, a dibenzothienylenyl group which may have a substituent, a phenyldibenzothienylenyl group which may have a substituent, a dibenzothienylenylphenyl group which may have a substituent, a pyridylenyl group which may have a substituent, a pyrimidinyl group which may have a substituent, a pyrazyl group which may have a substituent, a quinolyl group which may have a substituent, an isoquinolyl group which may have a substituent, a carbazolyl group which may have a substituent, a 9-phenylcarbazolyl group which may have a substituent, an acridinyl group which may have a substituent, a benzothiazolyl group which may have a substituent, a quinazolinyl group which may have a substituent, a quinoxalinyl group which may have a substituent, a 1,6-naphthyridinyl group which may have a substituent or a 1,8-naphthyridinyl group which may have a substituent.

The substituent on the aromatic hydrocarbon group which may have a substituent and the heteroaromatic group which may have a substituent is not particularly limited and may, for example, be a methyl group, an ethyl group, a $C_{3-18}$ alkyl group (such as a n-propyl group, an i-propyl group, a n-butyl group, a sec-butyl group, a tert-butyl group, a n-hexyl group, a cyclohexyl group, a cyclohexadienyl group, an octyl group, a benzyl group or a phenethyl group), a $C_{1-18}$ halogenated alkyl group (such as a trifluoromethyl group), a methoxy group, an ethoxy group, a $C_{3-18}$ alkoxy group (such as a n-propyloxy group, an i-propyloxy group, a n-butyloxy group, a sec-butyloxy group, a tert-butyloxy group, a n-hexyloxy group, a cyclohexyloxy group, a cyclohexadienyloxy group, an octyloxy group, a benzyloxy group or a phenethyloxy group), a $C_{1-18}$ halogenated alkoxy group (such as a trifluoromethoxy group), a phenyl group, a tolyl group, a pyridyl group, a pyrimidinyl group, a carbazolyl group, a dibenzothienyl group or a dibenzofuranyl group.

$Ar^1$ is, in view of excellent production efficiency of the aromatic compound, preferably a $C_{6-30}$ aromatic hydrocarbon group which may have a substituent or a $C_{3-30}$ heteroaromatic group which may have a substituent, more preferably a $C_{6-20}$ aromatic hydrocarbon group which may have a substituent or a $C_{3-20}$ heteroaromatic group which may have a substituent, and more specifically, further preferably a phenyl group, a biphenyl group, a naphthyl group, a terphenyl group, a dibenzofuranyl group, a phenyldibenzofuranyl group, a dibenzofuranylphenyl group, a dibenzothienylenyl group, a phenyldibenzothienylenyl group, a dibenzothienylenylphenyl group, a pyridyl group, a phenylpyridyl group, a pyridylphenyl group, a pyrimidinyl group, a pyrazyl group, a quinolyl group, an isoquinolyl group, a carbazolyl group or a 9-phenylcarbazolyl group (such a substituent may further be substituted with a methyl group, a butyl group, a hexyl group, an octyl group, a methoxy group, a phenyl group, a tolyl group, a pyridyl group, a pyridyl group, a pyrimidinyl group, a carbazolyl group, a dibenzothienyl group or a dibenzofuranyl group), still more preferably a phenyl group, a biphenyl group, a naphthyl group, a dibenzofuranyl group, a phenyldibenzofuranyl group, a dibenzofuranylphenyl group, a dibenzothienyl group, a phenyldibenzothienylenyl group, a dibenzothienylenylphenyl group, a pyridyl group, a quinolyl group or a carbazolyl group (such a substituent may further be substituted with a methyl group, a butyl group, a hexyl group, an octyl group or a methoxy group).

The boronic acid compound is not particularly limited and may, for example, be an aliphatic boronic acid compound, an aromatic boronic acid compound or a heteroaromatic boronic acid compound. The boronic acid compound is not particularly limited and may, for example, be a compound of the following formula (2):

(2)

wherein $Ar^2$ is a $C_{1-18}$ alkyl group, an aromatic hydrocarbon group which may have a substituent, or a heteroaromatic group which may have a substituent, $R^1$ is each independently a hydrogen atom, a $C_{1-4}$ alkyl group or a phenyl group, and the two $R^1$ may be linked to form a ring containing oxygen atoms and a boron atom.

The $C_{1-18}$ alkyl group is not particularly limited and may, for example, be a methyl group, an ethyl group, a n-propyl group, an i-propyl group, a n-butyl group, a sec-butyl group, a tert-butyl group, a n-hexyl group, a cyclohexyl group, a cyclohexadienyl group, an octyl group, a benzyl group or a phenethyl group.

The aromatic hydrocarbon group which may have a substituent and the heteroaromatic group which may have a substituent are respectively the same as the aromatic hydrocarbon group which may have a substituent and the heteroaromatic group which may have a substituent in $Ar^1$.

$Ar^2$ is, in view of excellent production efficiency of the aromatic compound, preferably a $C_{1-18}$ alkyl group, a $C_{6-30}$ aromatic hydrocarbon group which may have a substituent or a $C_{3-30}$ heteroaromatic group which may have a substituent, more preferably a $C_{1-18}$ alkyl group, a $C_{6-20}$ aromatic hydrocarbon group which may have a substituent or a $C_{3-20}$ heteroaromatic group which may have a substituent, and more specifically, further preferably a phenyl group, a biphenyl group, a naphthyl group, a terphenyl group, a dibenzofuranyl group, a phenyldibenzofuranyl group, a dibenzofuranylphenyl group, a dibenzothienylenyl group, a phenyldibenzothienylenyl group, a dibenzothienylenylphenyl group, a pyridyl group, a phenylpyridyl group, a pyridylphenyl group, a pyrimidinyl group, a pyrazyl group, a quinolyl group, an isoquinolyl group, a carbazolyl group or a 9-phenylcarbazolyl group (such a substituent may further be substituted with a methyl group, a butyl group, a hexyl group, an octyl group, a methoxy group, a phenyl group, a tolyl group, a pyridyl group, a pyrimidinyl group, a carbazolyl group, a dibenzothienyl group or a dibenzofuranyl group), still more preferably a phenyl group, a biphenyl group, a naphthyl group, a dibenzofuranyl group, a phenyldibenzofuranyl group, a dibenzofuranylphenyl group, a dibenzothienyl group, a phenyldibenzothienylenyl group, a dibenzothienylenylphenyl group, a pyridyl group, a quinolyl group or a carbazolyl group (such a substituent may further be substituted with a methyl group, a butyl group, a hexyl group, an octyl group or a methoxy group).

In the present invention, in a case where a compound represented by the above formula (1) and a compound represented by the above formula (2) are used, an aromatic compound represented by the following formula (3) is obtained:

(3)

wherein $Ar^1$, $Ar^2$ and n are the same as defined in the formulae (1) and (2).

In the present invention, since a nitro group leaves, a bond is newly formed on the carbon atom to which the nitro group has been bonded.

In the production method of the present invention, the molar ratio of the aromatic nitro compound (mol) to the boronic acid compound (mol) is not particularly limited, and is preferably within a range of from 0.1 to 10.0. From the viewpoint of economical efficiency, the molar ratio is more preferably from 0.2 to 5.0, further preferably from 0.33 to 3.0, still more preferably from 0.5 to 2.0.

n is an integer of from 1 to 5. With a view to synthesizing a desired aromatic compound with high selectivity, it is preferably an integer of from 1 to 3, more preferably an integer of from 1 to 2.

The metal catalyst is not particularly limited and may, for example, be a palladium catalyst or a nickel catalyst. The palladium catalyst is not particularly limited and may, for example, be a divalent palladium compound such as palladium(II) chloride, palladium(II) bromide, palladium(II)

acetate, palladium(II) acetylacetonate, bis(benzonitro)palladium(II) chloride, bis(acetonitrile)palladium(II) chloride, bis(triphenylphosphine)palladium(II) chloride, tetraamminepalladium(II) chloride, (cycloocta-1, 5-diene)palladium(II) chloride or palladium(II) trifluoroacetate, or a zerovalent palladium compound such as tris(dibenzylideneacetone)dipalladium(0), tris(dibenzylideneacetone)dipalladium(0) chloroform complex or tetrakis(triphenylphosphine)palladium(0). Further, a fixed palladium catalyst such as a polymer-fixed palladium catalyst or palladium carbon may also be mentioned. In such a palladium catalyst, a ligand compound such as a phosphine compound may coexist. Such a ligand compound is not particularly limited and may, for example, be a monodentate arylphosphine such as triphenylphosphine, tri(o-tolyl)phosphine or tri(mesityl)phosphine, a monodentate alkylphosphine such as tri(cyclohexyl)phosphine, tri(isopropyl)phosphine or tri(tert-butyl) phosphine, a Buchwald phosphine ligand such as 2-dicyclohexylphosphino-2',6'-dimethoxybiphenyl, 2-dicyclohexylphosphino-2',6'-diisopropoxybiphenyl, 2-dicyclohexylphosphino-2'-methylbiphenyl, 2-dicyclohexylphosphino-2',4',6'-triisopropylbiphenyl, 2-(di-tert-butylphosphino)-2',4',6'-triisopropylbiphenyl, 2-dicyclohexylphosphino-3,6-dimethoxy-2',4',6'-triisopropylbiphenyl, 2-(dicyclohexylphosphino)biphenyl, 2-(di-tert-butylphosphino)-2'-(N,N-dimethylamino)biphenyl or 2-dicyclohexylphosphino-2'-(N,N-dimethylamino)biphenyl, a bidentate phosphine such as 1,2-bis(diphenylphosphino)ethane, 1,2-bis(diphenylphosphino)propane, 1,2-bis(dicyclohexylphosphino)ethane, 1,2-bis(diphenylphosphino)butane or 1,2-bis(diphenylphosphino)ferrocene, or a N-heterocarbene ligand such as 1,3-bis(2,6-diisopropylphenyl)-4,5-dihydro-1H-imidazolium chloride, 1,3-bis(2,6-diisopropylphenyl)imidazolium chloride, or 1,3-bis(2,4,6-trimethylphenyl)-4,5-dihydro-1H-imidazolium chloride. Further, in a case where a ligand compound such as a phosphine compound coexists in the palladium catalyst, the palladium compound and the phosphine compound or the N-heterocarbene compound may be preliminarily mixed and prepared and then used for reaction.

The nickel catalyst may, for example, be a compound comprising a nickel salt and the above phosphine. The nickel salt means a compound containing nickel element as an effective component, such as a zerovalent to divalent nickel salt. It may, for example, be specifically a nickel halide such as nickel(II) fluoride, nickel(II) chloride, nickel(II) bromide or nickel(II) iodide, an inorganic salt such as nickel(0) powder, nickel(II) sulfate, nickel(II) nitrate or nickel(II) perchlorate, or an organic acid nickel salt such as nickel(II) formate, nickel(II) oxalate, nickel(II) acetate, nickel(II) benzoate or nickel(II) acetylacetonate.

Among such metal catalysts, with a view to making the desired reaction proceed, a palladium catalyst is preferred.

Further, with a view to making the desired reaction proceed highly selectively, it is preferred that in the metal catalyst, the Buchwald phosphine ligand coexists, and among the ligands, 2-dicyclohexylphosphino-3,6-dimethoxy-2',4',6'-triisopropylbiphenyl is particularly preferred.

The Buchwald phosphine ligand is not particularly limited and may, for example, be a phosphine compound represented by the following formula (4):

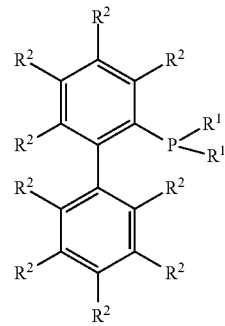

(4)

wherein $R^1$ is each independently a cyclohexyl group or a tert-butyl group. $R^2$ is each independently a hydrogen atom, a methyl group, a methoxy group, an isopropyl group, an isopropoxy group, a dimethylamino group or a sulfonic acid group.

The amount of the metal catalyst used is not particularly limited and is usually within a range of from 0.01 to 20 mol % per 1 mole of the aromatic nitro compound. When the amount of the metal catalyst is within the above range, an aromatic coupling reaction product can be formed with high selectivity, however, with a view to reducing the amount of the expensive metal catalyst, the amount of the metal catalyst used is more preferably within a range of from 0.01 to 10 mol % as calculated as metal per 1 mole of the atomic nitro compound.

In the present invention, a base is preferably used. The base used is selected from among inorganic bases and organic bases and is not particularly limited. It is preferably an inorganic base such as sodium hydroxide, potassium hydroxide, sodium carbonate, potassium carbonate, rubidium carbonate, cesium carbonate, potassium phosphate, sodium phosphate, potassium fluoride or cesium fluoride, an alkali metal alkoxide such as sodium methoxide, sodium ethoxide, potassium methoxide, potassium ethoxide, lithium tert-butoxide, sodium tert-butoxide or potassium tert-butoxide, or an organic base such as triethylamine, tributylamine, pyridine, diazabicycloundecene or diazabicyclononene, and with a view to improving the selectivity of the desired aromatic compound, it is preferably an inorganic base such as rubidium carbonate, cesium carbonate, potassium phosphate, sodium phosphate or cesium fluoride.

The amount of the base used is preferably at least 1.0 molar time the aromatic nitro compound used. If the amount of the base is less than 1.0 molar time, the yield of the desired aromatic coupling reaction may be low. Even if the base is added in large excess, the yield of the desired aromatic coupling reaction product will not change, however, the post-treatment after completion of the reaction will be complicated, and accordingly the amount of the base is more preferably within a range of from 1.0 to 5.0 molar times.

This reaction is carried out usually in the presence of an inert solvent. The solvent used is not particularly limited so long as it will not remarkably impair the reaction, and may, for example, be an aromatic organic solvent such as benzene, toluene or xylene, an ether organic solvent such as diethyl ether, diisopropyl ether, dibutyl ether, tetrahydrofuran, dimethoxyethane, 1,4-dioxane, cyclopentyl methyl ether, diethylene glycol dimethyl ether, diethylene glycol diethyl ether, diethylene glycol dibutyl ether or triethylene glycol dimethyl ether, acetonitrile, dimethylformamide, dimethylsulfoxide or hexamethylphosphotriamide. Among them, more preferred is an ether organic solvent such as diethyl ether, dimethoxyethane, diisopropyl ether, dibutyl ether, tetrahydrofuran, 1,4-dioxane, cyclopentyl methyl ether, diethylene glycol dimethyl ether, diethylene glycol diethyl ether, diethylene glycol dibutyl ether or triethylene glycol dimethyl ether.

This reaction may be carried out under normal pressure in an inert gas atmosphere of e.g. nitrogen or argon, or may be conducted under elevated pressure. The reaction is carried out at from 20 to 250° C., and in order to increase the yield of the desired aromatic compound, it is carried out preferably at from 50 to 200° C., more preferably from 100 to 160° C., further preferably from 120° C. to 150° C.

For this reaction, a phase transfer catalyst may be used as an additive. The phase transfer catalyst is not particularly limited and may, for example, be specifically a crown ether such as 24-crown-8, 18-crown-6, 15-crown-5 or 12-crown-4, or a quaternary ammonium salt such as tetra(n-butyl)ammonium chloride, tetra(n-butyl)ammonium bromide, benzyltriethylammonium chloride, triethyl-n-dodecylammonium chloride, triethyl-n-dodecylammonium bromide, trimethyl-n-hexadecylammonium chloride or trimethyl-n-hexadecylammonium bromide.

The reaction time for this reaction varies depending upon the amounts and the types of the aromatic nitro compound, the boronic acid compound, the metal catalyst and the base, the reaction temperature, etc., and is preferably within a range of from several minutes to 72 hours.

EXAMPLES

Now, the present invention will be described in further detail with reference to Examples. However, it should be understood that the present invention is by no means restricted thereto.

Measurement apparatus: gas chromatography GC2014 manufactured by Shimadzu Corporation (analysis conditions: column used: BP-1 manufactured by SGE Analytical Sciences, detector: FID at 290° C.), NMR: ECS-400 manufactured by JEOL Ltd. (1H NMR, 400 MHz; 13C NMR, 101 MHz), medium pressure column chromatography: Purifespoir 2 manufactured by Shoko Scientific Co., Ltd.

Example 1

In a stream of nitrogen, into a 15 mL screw vial, a stirrer, 92 mg (0.60 mmol) of 4-nitroanisole, 110 mg (0.90 mmol) of phenylboronic acid, 9.1 mg (0.030 mmol) of palladium(II) acetylacetonate, 64 mg (0.12 mmol) of 2-dicyclohexylphosphino-3,6-dimethoxy-2',4',6'-triisopropylbiphenyl, 480 mg (1.8 mmol) of tripotassium phosphate n-hydrate, 16 mg (0.060 mmol) of 18-crown-6 and 3 mL of 1,4-dioxane were added. The vial was tightly covered with a lid, followed by stirring with heating at 130° C. for 24 hours. Then, the reaction liquid was cooled to room temperature. Methylene chloride was added to the reaction liquid, and the reaction liquid was subjected to filtration through celite. The filtrate was concentrated, and the obtained residue was dissolved in diethyl ether (20 mL) and mixed with a 30% aqueous hydrogen peroxide solution (5 mL). The solution was stirred at room temperature for one hour, and washed with distilled water (10 mL) and a saturated aqueous iron(II) sulfate solution (10 mL). After extraction with diethyl ether (20 mL×3), the collected organic layer was washed with a saturated aqueous salt solution (10 mL). The organic layer was dried over anhydrous magnesium sulfate and concentrated, and the obtained residue was purified by medium pressure column chromatography (Biotage SNAP Ultra column (particle size: 25 μm), developing solvent: hexane/ethyl acetate) to obtain 84 mg (yield: 76%) of the desired 4-methoxybiphenyl as a white powder. The product was identified by 1H and 13C-NMR.

1H-NMR(CDCL3)=δ 7.59-7.51 (m, 4H), 7.42 (t, J=7.4 Hz, 2H), 7.31 (t, J=7.4 Hz, 1H), 6.99 (d, J=8.1 Hz, 2H), 3.86 (s, 3H)

13C-NMR(CDCL3)=δ 159.1, 140.8, 133.7, 128.7, 128.1, 126.7, 126.6, 114.2, 55.3.

Example 2

In a stream of nitrogen, into a 15 mL screw vial, a stirrer, 119 mg (0.60 mmol) of 4-nitrobiphenyl, 110 mg (0.90 mmol) of phenylboronic acid, 9.1 mg (0.030 mmol) of palladium(II) acetylacetonate, 64 mg (0.12 mmol) of 2-dicyclohexylphosphino-3,6-dimethoxy-2',4',6'-triisopropylbiphenyl, 270 mg (1.8 mmol) of cesium fluoride and 3 mL of 1,4-dioxane were added. The vial was tightly covered with a lid, followed by stirring with heating at 150° C. for 24 hours. Then, the reaction liquid was cooled to room temperature. Methylene chloride was added to the reaction liquid, and the reaction liquid was subjected to filtration through celite. The filtrate was concentrated, and the obtained residue was dissolved in diethyl ether (20 mL) and mixed with a 30% aqueous hydrogen peroxide solution (5 mL). The solution was stirred at room temperature for one hour, and washed with distilled water (10 mL) and a saturated aqueous iron(II) sulfate solution (10 mL). After extraction with diethyl ether (20 mL×3), the collected organic layer was washed with a saturated aqueous salt solution (10 mL). The organic layer was dried over anhydrous magnesium sulfate and concentrated, and the obtained residue was purified by medium pressure column chromatography (Biotage SNAP Ultra column (particle size: 25 μm), developing solvent: hexane/ethyl acetate) to obtain 90 mg (yield: 65%) of the desired p-terphenyl as a white powder. The product was identified by 1H and 13C-NMR.

1H-NMR(CDCL3)=δ 7.72-7.64 (m, 8H), 7.48 (t, J=7.5 Hz, 4H), 7.38 (t, J=7.3 Hz, 2H)

13C-NMR(CDCL3)=δ 140.7, 140.1, 128.8, 127.5, 127.3, 127.0.

Example 3

In a stream of nitrogen, into a 15 mL screw vial, a stirrer, 115 mg (0.60 mmol) of 4-(trifluoromethyl)nitrobenzene, 110 mg (0.90 mmol) of phenylboronic acid, 9.1 mg (0.030 mmol) of palladium(II) acetylacetonate, 64 mg (0.12 mmol) of 2-dicyclohexylphosphino-3,6-dimethoxy-2',4',6'-triisopropylbiphenyl, 270 mg (1.8 mmol) of cesium fluoride and 3 mL of 1,4-dioxane were added. The vial was tightly covered with a lid, followed by stirring with heating at 130° C. for 24 hours. Then, the reaction liquid was cooled to room temperature. Methylene chloride was added to the reaction liquid, and the reaction liquid was subjected to filtration through celite. The filtrate was concentrated, and the obtained residue was purified by medium pressure column chromatography (Biotage SNAP Ultra column (particle size: 25 μm), developing solvent: hexane/ethyl acetate) to obtain 74 mg (yield: 55%) of the desired 4-(trifluoromethyl)biphenyl as a white powder. The product was identified by 1H and 13C-NMR.

1H-NMR(CDCL3)=δ 7.70 (s, 4H), 7.61 (d, J=6.9 Hz, 2H), 7.48 (t, J=7.3 Hz, 2H), 7.42 (d, J=7.3 Hz, 1H)

13C-NMR(CDCL3)=144.7, 139.8, 129.3 (q, J=32.6 Hz), 129.0, 128.2, 127.4, 127.3, 125.7 (q, J=3.8 Hz), 124.2 (q, J=271.2 Hz).

Example 4

The same operation as in Example 2 was carried out except that 109 mg (0.60 mmol) of methyl 3-nitrobenzoate was used instead of 119 mg (0.60 mmol) of 4-nitrobiphenyl, whereupon 86 mg (yield: 68%) of methyl 3-phenylbenzoate as a colorless oily substance was obtained. The product was identified by 1H and 13C-NMR.

1H-NMR(CDCL3)=δ 8.29 (s, 1H), 8.03 (d, J=7.7 Hz, 1H), 7.79 (d, J=7.7 Hz, 1H), 7.63 (d, J=8.1 Hz, 2H), 7.52 (t, J=7.7 Hz, 1H), 7.47 (t, J=7.7 Hz, 2H), 7.39 (t, J=7.0 Hz, 1H), 3.95 (s, 3H)

13C-NMR(CDCL3)=δ 167.0, 141.4, 140.1, 131.5, 130.6, 128.9, 128.8, 128.3, 128.2, 127.7, 127.1, 52.2.

Example 5

In a stream of nitrogen, into a 15 mL screw vial, a stirrer, 95 mg (0.60 mmol) of 3,5-difluoronitrobenzene, 110 mg (0.90 mmol) of phenylboronic acid, 9.1 mg (0.030 mmol) of palladium(II) acetylacetonate, 64 mg (0.12 mmol) of 2-dicyclohexylphosphino-3,6-dimethoxy-2',4',6'-triisopropylbiphenyl, 270 mg (1.8 mmol) of cesium fluoride and 3 mL of 1,4-dioxane were added. The vial was tightly covered with a lid, followed by stirring with heating at 130° C. for 24 hours. Then, the reaction liquid was cooled to room temperature. Methylene chloride was added to the reaction liquid, and the reaction liquid was subjected to filtration through celite. The filtrate was concentrated, and the obtained residue was purified by medium pressure column chromatography (Biotage SNAP Ultra column (particle size: 25 µm), developing solvent: hexane/ethyl acetate) to obtain 86 mg (yield: 68%) of 3,5-difluorobiphenyl as a colorless oily substance. The product was identified by 1H and 13C-NMR.

1H-NMR(CDCL3)=δ 7.55 (d, J=7.8 Hz, 2H), 7.46 (t, J=7.3 Hz, 2H), 7.40 (tt, J=6.9, 1.4 Hz, 1H), 7.11 (dd, J=8.7, 2.3 Hz, 2H), 6.79 (tt, J=8.7, 2.3 Hz, 1H)

13C-NMR(CDCL3)=δ 163.3 (dd, J=247.8, 12.9 Hz), 144.5 (t, J=9.1 Hz), 138.9, 129.0, 128.4, 127.0, 109.9 (dd, J=19.2, 6.7 Hz), 102.5 (t, J=25.9 Hz).

Example 6

In a stream of nitrogen, into a 15 mL screw vial, a stirrer, 104 mg (0.60 mmol) of 1-nitronaphthalene, 110 mg (0.90 mmol) of phenylboronic acid, 9.1 mg (0.030 mmol) of palladium(II) acetylacetonate, 64 mg (0.12 mmol) of 2-dicyclohexylphosphino-3,6-dimethoxy-2',4',6'-triisopropylbiphenyl, 480 mg (1.8 mmol) of tripotassium phosphate n-hydrate and 3 mL of 1,4-dioxane were added. The vial was tightly covered with a lid, followed by stirring with heating at 130° C. for 12 hours. Then, the reaction liquid was cooled to room temperature. Methylene chloride was added to the reaction liquid, and the reaction liquid was subjected to filtration through celite. The filtrate was concentrated, and the obtained residue was purified by medium pressure column chromatography (Biotage SNAP Ultra column (particle size: 25 µm), developing solvent: hexane/ethyl acetate) to obtain 101 mg (yield: 82%) of the desired 1-phenylnaphthalene as a colorless oily substance. The product was identified by 1H and 13C-NMR.

1H-NMR(CDCL3)=δ 7.97-7.87 (m, 3H), 7.59-7.42 (m, 9H)

13C-NMR(CDCL3)=δ 140.7, 140.2, 133.7, 131.6, 130.0, 128.2, 127.6, 127.2, 126.9, 126.0, 125.7, 125.3.

Example 7

The same operation as in Example 6 was carried out except that 104 mg (0.60 mmol) of 2-nitronaphthalene was used instead of 104 mg (0.60 mmol) of 1-nitronaphthalene, whereupon 100 mg (yield: 81%) of 2-phenylnaphthalene as a white powder was obtained. The product was identified by 1H and 13C-NMR.

1H-NMR(CDCL3)=δ 8.06 (s, 1H), 7.92 (t, J=8.7 Hz, 2H), 7.88 (d, J=7.4 Hz, 1H), 7.79-7.71 (m, 3H), 7.55-7.46 (m, 4H), 7.40 (t, J=7.0 Hz, 1H)

13C-NMR(CDCL3)=δ 141.1, 138.5, 133.6, 132.6, 128.8, 128.4, 128.2, 127.6, 127.4, 127.3, 126.3, 125.9, 125.8, 125.6.

Example 8

The same operation as in Example 6 was carried out except that 74 mg (0.60 mmol) of 3-nitropyridine was used instead of 104 mg (0.60 mmol) of 1-nitronaphthalene, whereupon 73 mg (yield: 79%) of 3-phenylpyridine as a colorless oily substance was obtained. The product was identified by 1H and 13C-NMR.

1H-NMR(CDCL3)=δ 8.86 (bs, 1H), 8.59 (d, J=4.7 Hz, 1H), 7.87 (bd, J=8.1 Hz, 1H), 7.59 (d, J=8.1 Hz, 2H), 7.48 (t, J=7.4 Hz, 2H), 7.45-7.33 (m, 2H)

13C-NMR(CDCL3)=δ 148.5, 148.3, 137.8, 136.6, 134.3, 129.0, 128.1, 127.1, 123.5.

Example 9

The same operation as in Example 1 was carried out except that 122 mg (0.90 mmol) of 4-methylphenylboronic acid was used instead of 110 mg (0.90 mmol) of phenylboronic acid and that 18-crown-6 was not added, whereupon 95 mg (yield: 79%) of 4-methyl-4'-methoxybiphenyl as a white solid was obtained. The product was identified by 1H and 13C-NMR.

1H-NMR(CDCL3)=δ 7.52 (d, J=8.7 Hz, 2H), 7.45 (d, J=7.4 Hz, 2H), 7.23 (d, J=8.1 Hz, 2H), 6.97 (d, J=8.1 Hz, 2H), 3.85 (s, 3H), 2.39 (s, 3H)

13C-NMR(CDCL3)=δ 158.9, 137.9, 136.3, 133.7, 129.4, 127.9, 126.6, 114.1, 55.3, 21.0.

Example 10

The same operation as in Example 1 was carried out except that 126 mg (0.90 mmol) of 4-fluorophenylboronic acid was used instead of 110 mg (0.90 mmol) of phenylboronic acid and that 18-crown-6 was not added, whereupon 88 mg (yield: 73%) of 4-fluoro-4'-methoxybiphenyl as a white solid was obtained. The product was identified by 1H and 13C-NMR.

1H-NMR(CDCL3)=δ 7.54-7.45 (m, 4H), 7.16-7.07 (m, 2H), 6.99 (d, J=8.7 Hz, 2H), 3.86 (s, 3H)

13C-NMR(CDCL3)=δ 162.0 (d, J=245.4 Hz), 159.1, 136.9 (d, J=2.9 Hz), 132.8, 128.2 (d, J=8.6 Hz), 128.0, 115.5 (d, J=21.1 Hz), 114.2, 55.3.

Example 11

The same operation as in Example 1 was carried out except that 125 mg (0.60 mmol) of 4-(4-nitrophenyl)morpholine was used instead of 92 mg (0.60 mmol) of 4-nitroanisole, whereupon 90 mg (yield: 63%) of 4-(1,1'-biphenyl-4-yl)morpholine as a white solid was obtained. The product was identified by 1H and 13C-NMR.

1H-NMR(CDCL3)=δ 7.63-7.54 (m, 4H), 7.45 (t, J=7.4 Hz, 2H), 7.33 (t, J=7.4 Hz, 1H), 7.01 (d, J=8.7 Hz, 2H), 3.91 (t, J=7.4 Hz, 4H), 3.23 (t, J=4.4 Hz, 4H)

13C-NMR(CDCL3)=δ 150.5, 140.7, 132.6, 128.6, 127.7, 126.6, 115.7, 66.8, 49.1.

Example 12

The same operation as in Example 1 was carried out except that 82 mg (0.60 mmol) of 4-nitrotoluene was used instead of 92 mg (0.60 mmol) of 4-nitroanisole and that 137 mg (0.90 mmol) of 4-methoxyphenylboronic acid was used instead of 110 mg (0.90 mmol) of phenylboronic acid, whereupon 93 mg (yield: 78%) of 4-methoxy-4'-methyl-1,1'-biphenyl as a white solid was obtained. The product was identified by 1H and 13C-NMR.

1H-NMR(CDCL3)=δ 7.52 (d, J=8.7 Hz, 2H), 7.46 (d, J=7.4 Hz, 2H), 7.23 (d, J=8.1 Hz, 2H), 6.97 (d, J=8.1 Hz, 2H), 3.85 (s, 3H), 2.39 (s, 3H)

13C-NMR(CDCL3)=δ 158.9, 137.9, 136.3, 133.7, 129.4, 127.9, 126.5, 114.1, 55.2, 21.0.

Example 13

The same operation as in Example 1 was carried out except that 62 μL (0.60 mmol) of nitrobenzene was used instead of 92 mg (0.60 mmol) of 4-nitroanisole and that 137 mg (0.90 mmol) of 4-methoxyphenylboronic acid was used instead of 110 mg (0.90 mmol) of phenylboronic acid, whereupon 93 mg (yield: 78%) of 4-methoxy-1,1'-biphenyl as a white solid was obtained. The product was identified by 1H and 13C-NMR, and the same spectrum data as those of the compound obtained in Example 1 were obtained.

Example 14

The same reaction as in Example 1 was carried out except that 117 mg (0.60 mmol) of 2-(4-nitrophenyl)-1,3-dioxolane was used instead of 92 mg (0.60 mmol) of 4-nitroanisole and that 137 mg (0.90 mmol) of 4-methoxyphenylboronic acid was used instead of 110 mg (0.90 mmol) of phenylboronic acid. Then, the reaction liquid was cooled to room temperature. To the reaction liquid, 3.0 mL of a 3N aqueous hydrochloric acid solution and 10 mL of isopropanol were added, followed by stirring with heating at 80° C. for 3 hours. Then, the reaction liquid was cooled to room temperature and neutralized, mixed with methylene chloride and subjected to filtration through celite. The filtrate was concentrated, and the obtained residue was dissolved in diethyl ether (20 mL) and mixed with a 30% aqueous hydrogen peroxide solution (5 mL). The solution was stirred at room temperature for one hour, and washed with distilled water (10 mL) and a saturated aqueous iron(II) sulfate solution (10 mL). After extraction with diethyl ether (20 mL×3), the collected organic layer was washed with a saturated aqueous salt solution (10 mL). The organic layer was dried over anhydrous magnesium sulfate and concentrated, and the obtained residue was purified by medium pressure column chromatography (Biotage SNAP Ultra column (particle size: 25 μm), developing solvent: hexane/ethyl acetate) to obtain 77 mg (yield: 61%) of the desired 4'-methoxy-[1,1'-biphenyl]-4-carbaldehyde as a white solid. The product was identified by 1H and 13C-NMR.

1H-NMR(CDCL3)=δ 10.03 (s, 1H), 7.93 (d, J=8.4 Hz, 2H), 7.72 (d, J=8.1 Hz, 2H), 7.60 (d, J=8.1 Hz, 2H), 7.01 (d, J=8.7 Hz, 2H), 3.87 (s, 3H)

13C-NMR(CDCL3)=δ 191.9, 160.1, 146.7, 134.6, 132.0, 130.3, 128.5, 127.0, 114.4, 55.3.

Example 15

The same reaction as in Example 1 was carried out except that 125 mg (0.60 mmol) of 2-methyl-2-(4-nitrophenyl)-1,3-dioxolane was used instead of 92 mg (0.60 mmol) of 4-nitroanisole. Then, the reaction liquid was cooled to room temperature. To the reaction liquid, 3.0 mL of a 3N aqueous hydrochloric acid solution and 10 mL of isopropanol were added, followed by stirring with heating at 80° C. for 3 hours. Then, the reaction liquid was cooled to room temperature and neutralized, mixed with methylene chloride and subjected to filtration through celite. The filtrate was concentrated, and the obtained residue was dissolved in diethyl ether (20 mL) and mixed with a 30% aqueous hydrogen peroxide solution (5 mL). The solution was stirred at room temperature for one hour, and washed with distilled water (10 mL) and a saturated aqueous iron(11) sulfate solution (10 mL). After extraction with diethyl ether (20 mL×3), the collected organic layer was washed with a saturated aqueous salt solution (10 mL). The organic layer was dried over anhydrous magnesium sulfate and concentrated, and the obtained residue was purified by medium pressure column chromatography (Biotage SNAP Ultra column (particle size: 25 μm), developing solvent: hexane/ethyl acetate) to obtain 85 mg (yield: 72%) of the desired 1-([1,1'-biphenyl]-4-yl)ethan-1-one as a white solid. The product was identified by 1H and 13C-NMR.

1H-NMR(CDCL3)=δ 8.04 (d, J=8.1 Hz, 2H), 7.69 (d, J=8.1 Hz, 2H), 7.63 (d, J=8.1 Hz, 2H), 7.48 (t, J=7.4 Hz, 2H), 7.41 (t, J=7.4 Hz, 1H), 2.64 (s, 3H)

13C-NMR(CDCL3)=δ 197.7, 145.7, 139.8, 135.7, 128.9, 128.8, 128.2, 127.2, 127.1, 26.6.

Example 16

The same operation as in Example 1 was carried out except that 115 mg (0.60 mmol) of 1-nitro-4-(trifluoromethyl)benzene was used instead of 92 mg (0.60 mmol) of 4-nitroanisole, that 182 mg (1.20 mmol) of 4-methoxyphenylboronic acid was used instead of 110 mg (0.90 mmol) of phenylboronic acid, that 0.27 g (1.8 mmol) of cesium fluoride was used instead of 480 mg (1.8 mmol) of tripotassium phosphate n-hydrate, that 18-crown-6 was not added, and that 3 mL of toluene was used instead of 3 mL of 1,4-dioxane, whereupon 82 mg (yield: 54%) of 4-methoxy-4'-(trifluoromethyl)-1,1'-biphenyl as a white solid was obtained. The product was identified by 1H, 13C and 19F-NMR.

1H-NMR(CDCL3)=δ 7.71-7.62 (m, 4H), 7.56 (d, J=8.7 Hz, 2H), 7.02 (d, J=8.7 Hz, 2H), 3.87 (s, 3H)

13C-NMR(CDCL3)=δ 159.8, 144.2, 132.1, 128.6 (q, J=32.6 Hz), 128.3, 126.8, 125.6 (q, J=3.8 Hz), 124.4 (q, J=272 Hz), 114.4, 55.3

19F-NMR(CDCL3)=δ 62.16.

Example 17

The same operation as in Example 1 was carried out except that 85 mg (0.60 mmol) of 1-fluoro-4-nitrobenzene was used instead of 92 mg (0.60 mmol) of 4-nitroanisole, that 137 mg (0.90 mmol) of 4-methoxyphenylboronic acid was used instead of 110 mg (0.90 mmol) of phenylboronic acid, that 0.46 g (3.0 mmol) of cesium fluoride was used instead of 480 mg (1.8 mmol) of tripotassium phosphate n-hydrate, that 18-crown-6 was not added, and that 3 mL of toluene was used instead of 3 mL of 1,4-dioxane, whereupon 56 mg (yield: 46%) of 4-fluoro-4'-methoxy-1,1'-biphenyl as a white solid was obtained. The product was identified by 1H, 13C and 19F-NMR.

1H-NMR(CDCL3)=δ 7.54-7.45 (m, 4H), 7.16-7.07 (m, 2H), 6.99 (d, J=8.7 Hz, 2H), 3.86 (s, 3H)

13C-NMR(CDCL3)=δ 162.0 (d, J=245.4 Hz), 159.1, 136.9 (d, J=2.9 Hz), 132.8, 128.2 (d, J=8.6 Hz), 128.0, 115.5 (d, J=21.1 Hz), 114.2, 55.3

19F-NMR(CDCL3)=δ 116.59.

Example 18

The same operation as in Example 1 was carried out except that 92 mg (0.60 mmol) of 3-nitroanisole was used instead of 92 mg (0.60 mmol) of 4-nitroanisole, whereupon 82 mg (yield: 74%) of 3-methoxy-1,1'-biphenyl as a colorless transparent oil was obtained. The product was identified by 1H and 13C-NMR.

1H-NMR(CDCL3)=δ 7.61 (d, J=8.1 Hz, 2H), 7.45 (t, J=7.4 Hz, 2H), 7.42-7.33 (m, 2H), 7.20 (d, J=7.4 Hz, 1H), 7.15 (s, 1H), 6.92 (d, J=7.4 Hz, 1H), 3.88 (s, 3H)

13C-NMR(CDCL3)=δ 159.9, 142.7, 141.1, 129.7, 128.7, 127.4, 127.2, 119.7, 112.9, 112.6, 55.3.

Example 19

The same operation as in Example 1 was carried out except that 91 mg (0.60 mmol) of 1,3-dimethyl-5-nitrobenzene was used instead of 92 mg (0.60 mmol) of 4-nitroanisole and that 182 mg (1.20 mmol) of 4-methoxyphenylboronic acid was used instead of 110 mg (0.90 mmol) of phenylboronic acid, whereupon 90 mg (yield: 71%) of 4'-methoxy-3,5-dimethyl-1,1'-biphenyl as a white solid was obtained. The product was identified by 1H and 13C-NMR.

1H-NMR(CDCL3)=δ 7.52 (d, J=8.7 Hz, 2H), 7.18 (s, 2H), 7.00-6.94 (m, 3H), 3.86 (s, 3H), 2.38 (s, 6H)

13C-NMR(CDCL3)=δ 159.0, 140.8, 138.2, 134.0, 128.3, 128.1, 124.7, 114.0, 55.3, 21.4.

Example 20

The same operation as in Example 1 was carried out except that 121 mg (0.60 mmol) of 1-(methanesulfonyl)-3-nitrobenzene was used instead of 92 mg (0.60 mmol) of 4-nitroanisole, whereupon 91 mg (yield: 65%) of 3-(methanesulfonyl)-1,1'-biphenyl as a white solid was obtained. The product was identified by 1H and 13C-NMR.

1H-NMR(CDCL3)=δ 8.16 (s, 1H), 7.89 (dd, J=19.5, 8.1 Hz, 2H), 7.68-7.58 (m, 3H), 7.48 (t, J=7.4 Hz, 2H), 7.42 (t, J=7.4 Hz, 1H), 3.10 (s, 3H)

13C-NMR(CDCL3)=δ 142.6, 141.0, 138.9, 132.2, 129.8, 129.0, 128.3, 127.1, 125.8, 125.7, 44.4.

Example 21

The same operation as in Example 1 was carried out except that 82 mg (0.60 mmol) of 2-nitrotoluene was used instead of 92 mg (0.60 mmol) of 4-nitroanisole and that 137 mg (0.90 mmol) of 4-methoxyphenylboronic acid was used instead of 110 mg (0.90 mmol) of phenylboronic acid, whereupon 81 mg (yield: 68%) of 4-methoxy-2'-methyl-1, 1'-biphenyl as a colorless transparent oil was obtained. The product was identified by 1H and 13C-NMR.

1H-NMR(CDCL3)=δ 7.29-7.20 (m, 6H), 6.95 (d, J=8.7 Hz, 2H), 3.85 (s, 3H), 2.28 (s, 3H)

13C-NMR(CDCL3)=δ 158.5, 141.5, 135.5, 134.3, 130.3, 130.2, 129.9, 126.9, 125.7, 113.4, 55.3, 20.5.

Example 22

The same operation as in Example 1 was carried out except that 92 mg (0.60 mmol) of 2-nitroanisole was used instead of 92 mg (0.60 mmol) of 4-nitroanisole, whereupon 93 mg (yield: 84%) of 2-methoxy-1,1'-biphenyl as a colorless transparent oil was obtained. The product was identified by 1H and 13C-NMR.

1H-NMR(CDCL3)=δ 7.58-7.52 (m, 2H), 7.42 (t, J=7.4 Hz, 2H), 7.38-7.30 (m, 3H), 7.04 (t, J=7.4 Hz, 1H), 7.00 (d, J=8.7 Hz, 1H), 3.82 (s, 3H).

13C-NMR(CDCL3)=δ 156.4, 138.5, 130.9, 130.7, 129.5, 128.6, 127.9, 126.9, 120.8, 112.2, 55.5.

Example 23

The same operation as in Example 1 was carried out except that 134 mg (0.60 mmol) of 9-nitroanthracene was used instead of 92 mg (0.60 mmol) of 4-nitroanisole, that 0.46 g (3.0 mmol) of cesium fluoride was used instead of 480 mg (1.8 mmol) of tripotassium phosphate n-hydrate, that 18-crown-6 was not added, and that 3 mL of toluene was used instead of 3 mL of 1,4-dioxane, whereupon 67 mg (yield: 44%) of 9-phenylanthracene as a white solid was obtained. The product was identified by 1H and 13C-NMR.

1H-NMR(CDCL3)=δ 8.53 (s, 1H), 8.08 (d, J=8.1 Hz, 2H), 7.72 (d, J=9.4 Hz, 2H), 7.66-7.55 (m, 3H), 7.53-7.45 (m, 4H), 7.42-7.35 (m, 2H)

13C-NMR(CDCL3)=δ 138.7, 137.0, 131.3, 131.2, 130.2, 128.32, 128.30, 127.4, 126.8, 126.5, 125.3, 125.1.

Example 24

The same operation as in Example 1 was carried out except that 92 mg (0.60 mmol) of 2-methoxy-3-nitropyridine was used instead of 92 mg (0.60 mmol) of 4-nitroanisole, whereupon 89 mg (yield: 80%) of 2-methoxy-3-phenylpyridine as a colorless transparent oil was obtained. The product was identified by 1H and 13C-NMR.

1H-NMR(CDCL3)=δ 8.18 (dd, J=4.7, 1.3 Hz, 1H), 7.62 (dd, J=7.4, 1.3 Hz, 1H), 7.57 (d, J=8.1 Hz, 2H), 7.44 (t, J=7.7 Hz, 2H), 7.36 (t, J=7.0 Hz, 1H), 6.98 (dd, J=6.7, 4.7 Hz, 1H), 3.98 (s, 3H)

13C-NMR(CDCL3)=δ 160.8, 145.7, 138.6, 136.7, 129.1, 128.2, 127.5, 124.6, 117.1, 53.5.

Example 25

The same operation as in Example 1 was carried out except that 104 mg (0.60 mmol) of 5-nitroquinoline was used instead of 92 mg (0.60 mmol) of 4-nitroanisole and that 18-crown-6 was not added, whereupon 87 mg (yield: 71%) of 5-phenylquinoline as a pale yellow solid was obtained. The product was identified by 1H and 13C-NMR.

1H-NMR(CDCL3)=δ 8.95-8.90 (m, 1H), 8.24 (d, J=8.7, 1H), 8.14 (d, J=8.7 Hz, 1H), 7.76 (t, J=8.1 Hz, 1H), 7.55-7.41 (m, 6H), 7.34 (dd, J=8.7, 4.4 Hz, 1H)

13C-NMR(CDCL3)=δ 150.2, 148.5, 140.4, 139.3, 134.3, 130.0, 128.92, 128.86, 128.4, 127.6, 127.2, 126.6, 121.0.

Example 26

The same operation as in Example 1 was carried out except that 104 mg (0.60 mmol) of 5-nitroisoquinoline was used instead of 92 mg (0.60 mmol) of 4-nitroanisole, whereupon 86 mg (yield: 70%) of 5-phenylisoquinoline as a yellow oil was obtained. The product was identified by 1H and 13C-NMR.

1H-NMR(CDCL3)=δ 9.31 (s, 1H), 8.47 (d, J=5.4, 1H), 7.97 (t, J=4.4 Hz, 1H), 7.72 (d, J=6.0 Hz, 1H), 7.64 (d, J=4.0 Hz, 2H), 7.54-7.41 (m, 5H)

13C-NMR(CDCL3)=δ 152.6, 143.1, 139.1, 138.8, 134.0, 130.9, 129.7, 128.8, 128.4, 127.7, 127.1, 126.8, 118.5.

Example 27

The same operation as in Example 1 was carried out except that 160 mg (0.90 mmol) of 4-tert-butylphenylboronic acid was used instead of 110 mg (0.90 mmol) of phenylboronic acid, whereupon 116 mg (yield: 80%) of 4-(tert-butyl)-4'-methoxy-1,1'-biphenyl as a white solid was obtained. The product was identified by 1H and 13C-NMR.

1H-NMR(CDCL3)=δ 7.60-7.52 (m, 4H), 7.51-7.46 (m, 2H), 7.01 (d, J=8.1, 2H), 3.88 (s, 3H), 1.41 (s, 9H)

13C-NMR(CDCL3)=δ 158.9, 149.6, 137.9, 133.6, 128.0, 126.3, 125.6, 114.1, 55.3, 34.4, 31.4.

Example 28

The same operation as in Example 1 was carried out except that 62 μL (0.60 mmol) of nitrobenzene was used instead of 92 mg (0.60 mmol) of 4-nitroanisole and that 178 mg (0.90 mmol) of [1,1'-biphenyl]-4-yl-boronic acid was used instead of 110 mg (0.90 mmol) of phenylboronic acid, whereupon 91 mg (yield: 66%) of p-terphenyl as a white powder was obtained. The product was identified by 1H and 13C-NMR, and the same spectrum data as those of the compound obtained in Example 2 were obtained.

Example 29

The same operation as in Example 1 was carried out except that 92 mg (0.60 mmol) of 2-nitroanisole was used instead of 92 mg (0.60 mmol) of 4-nitroanisole and that 197 mg (1.20 mmol) of 4-acetylphenylboronic acid was used instead of 110 mg (0.90 mmol) of phenylboronic acid, whereupon 91 mg (yield: 66%) of 1-(2'-methoxy-[1,1'-biphenyl]-4-yl)ethan-1-one as a white solid was obtained. The product was identified by 1H and 13C-NMR.

1H-NMR(CDCL3)=δ 8.01 (bd, J=7.4 Hz, 2H), 7.65 (bd, J=8.1 Hz, 2H), 7.42-7.32 (m, 2H), 7.06 (t, J=7.4 Hz, 1H), 7.01 (d, J=8.1 Hz, 1H), 3.83 (s, 3H), 2.64 (s, 3H)

13C-NMR(CDCL3)=δ 197.8, 156.4, 143.5, 135.4, 130.6, 129.6, 129.4, 129.3, 128.0, 120.9, 111.2, 55.5, 26.6.

Example 30

The same operation as in Example 1 was carried out except that 92 mg (0.60 mmol) of 2-nitroanisole was used instead of 92 mg (0.60 mmol) of 4-nitroanisole and that 162 mg (0.90 mmol) of 4-(methoxycarbonyl)phenylboronic acid was used instead of 110 mg (0.90 mmol) of phenylboronic acid, whereupon 95 mg (yield: 66%) of methyl 2'-methoxy-[1,1'-biphenyl]-4-carboxylate as a white solid was obtained. The product was identified by 1H and 13C-NMR.

1H-NMR(CDCL3)=δ 8.09 (d, J=8.7 Hz, 2H), 7.62 (d, J=8.1 Hz, 2H), 7.41-7.32 (m, 2H), 7.06 (t, J=7.7 Hz, 1H), 7.01 (d, J=8.1 Hz, 1H), 3.94 (s, 3H), 3.82 (s, 3H)

13C-NMR(CDCL3)=δ 167.1, 156.4, 143.3, 130.7, 129.5, 129.3, 129.2, 128.4, 120.9, 111.3, 55.5, 52.0.

Example 31

The same operation as in Example 1 was carried out except that 92 mg (0.60 mmol) of 2-nitroanisole was used instead of 92 mg (0.60 mmol) of 4-nitroanisole and that 171 mg (0.90 mmol) of 4-(trifluoromethyl)phenylboronic acid was used instead of 110 mg (0.90 mmol) of phenylboronic acid, whereupon 98 mg (yield: 65%) of 2-methoxy-4'-(trifluoromethyl)-1,1'-biphenyl as a colorless transparent oil was obtained. The product was identified by 1H, 13C and 19F-NMR.

1H-NMR(CDCL3)=δ 7.74-7.66 (m, 4H), 7.42 (t, J=7.7 Hz, 1H), 7.36 (d, J=7.4 Hz, 1H), 7.12 (t, J=7.4 Hz, 1H), 7.05 (d, J=8.1 Hz, 1H), 3.86 (s, 3H)

13C-NMR(CDCL3)=δ 156.4, 142.2, 130.7, 129.8, 129.5, 129.1, 128.9 (q, J=32.6 Hz), 124.8 (q, J=3.8 Hz), 124.4 (q, J=272.2 Hz), 120.9, 111.3, 55.5

19F-NMR(CDCL3)=δ 62.8.

Example 32

The same operation as in Example 1 was carried out except that 109 mg (0.60 mmol) of methyl 3-nitrobenzoate was used instead of 92 mg (0.60 mmol) of 4-nitroanisole, that 171 mg (0.90 mmol) of 4-(trifluoromethyl)phenylboronic acid was used instead of 110 mg (0.90 mmol) of phenylboronic acid, that 0.46 g (3.0 mmol) of cesium fluoride was used instead of 480 mg (1.8 mmol) of tripotassium phosphate n-hydrate, and that 18-crown-6 was not added, whereupon 106 mg (yield: 63%) of methyl 4'-(trifluoromethyl)-1,1'-biphenyl-3-carboxylate as a colorless transparent oil was obtained. The product was identified by 1H, 13C and 19F-NMR.

1H-NMR(CDCL3)=δ 8.29 (bs, 1H), 8.08 (d, J=8.1 Hz, 1H), 7.79 (d, J=7.4 Hz, 1H), 7.76-7.70 (m, 4H), 7.55 (t, J=8.1 Hz, 1H), 3.96 (s, 3H)

13C-NMR(CDCL3)=δ 166.8, 143.6, 140.0, 131.6, 130.9, 129.8 (q, J=32.6 Hz), 129.2, 129.1, 128.4, 127.5, 125.8 (q, J=3.8 Hz), 124.2 (q, J=272.2 Hz), 52.3

19F-NMR(CDCL3)=δ 62.4.

Example 33

The same operation as in Example 1 was carried out except that 74 mg (0.60 mmol) of nitrobenzene was used instead of 92 mg (0.60 mmol) of 4-nitroanisole, and that 137 mg (0.90 mmol) of 3-methoxyphenylboronic acid was used instead of 110 mg (0.90 mmol) of phenylboronic acid, whereupon 79 mg (yield: 72%) of 3-methoxy-1,1'-biphenyl as a colorless transparent oil was obtained. The product was identified by 1H and 13C-NMR.

1H-NMR(CDCL3)=δ 7.60 (d, J=8.1 Hz, 2H), 7.45 (t, J=7.4 Hz, 2H), 7.42-7.32 (m, 2H), 7.20 (d, J=8.1 Hz, 1H), 7.14 (s, 1H), 6.92 (d, J=8.1 Hz, 1H), 3.89 (s, 3H)

13C-NMR(CDCL3)=δ 159.9, 142.7, 141.1, 129.7, 128.7, 127.4, 127.2, 119.7, 112.9, 112.6, 55.3.

Example 34

The same operation as in Example 1 was carried out except that 92 mg (0.60 mmol) of 2-nitroanisole was used instead of 92 mg (0.60 mmol) of 4-nitroanisole, and that 122 mg (0.90 mmol) of o-tolylboronic acid was used instead of 110 mg (0.90 mmol) of phenylboronic acid, whereupon 79 mg (yield: 67%) of 2-methoxy-2'-methyl-1,1'-biphenyl as a colorless transparent oil was obtained. The product was identified by 1H and 13C-NMR.

1H-NMR(CDCL3)=δ 7.34 (t, J=8.1 Hz, 1H), 7.28-7.12 (m, 5H), 7.01 (t, J=7.4 Hz, 1H), 6.96 (d, J=8.1 Hz, 1H), 3.76 (s, 3H)), 2.14 (s, 3H)

13C-NMR(CDCL3)=δ 156.6, 138.6, 136.8, 131.0, 130.8, 130.0, 129.6, 128.5, 127.3, 125.4, 120.4, 110.6, 55.4, 19.9.

Example 35

The same operation as in Example 1 was carried out except that 104 mg (0.60 mmol) of 1-nitronaphthalene was used instead of 92 mg (0.60 mmol) of 4-nitroanisole and that 135 mg (0.90 mmol) of 2,6-dimethylphenylboronic acid was used instead of 110 mg (0.90 mmol) of phenylboronic acid, whereupon 50 mg (yield: 36%) of 1-(2,6-dimethylphenyl)naphthalene as a white solid was obtained. The product was identified by 1H and 13C-NMR.

1H-NMR(CDCL3)=δ 7.91 (d, J=7.8 Hz, 1H), 7.86 (d, J=8.2 Hz, 1H), 7.55 (t, J=7.8 Hz, 1H), 7.47 (t, J=6.9 Hz, 1H), 7.38-7.32 (m, 2H), 7.30-7.22 (m, 2H), 7.20-7.16 (m, 2H), 1.91 (s, 6H)

13C-NMR(CDCL3)=δ 139.6, 138.7, 137.0, 133.7, 131.7, 128.3, 127.3, 127.24, 127.17, 126.4, 126.0, 125.75, 125.68, 125.3, 20.4.

Example 36

The same operation as in Example 1 was carried out except that 92 mg (0.60 mmol) of 2-nitroanisole was used instead of 92 mg (0.60 mmol) of 4-nitroanisole and that 155 mg (0.90 mmol) of 2-naphthaleneboronic acid was used instead of 110 mg (0.90 mmol) of phenylboronic acid, whereupon 113 mg (yield: 81%) of 2-(2-methoxyphenyl)naphthalene as a white solid was obtained. The product was identified by 1H and 13C-NMR.

1H-NMR(CDCL3)=δ 8.04 (s, 1H), 7.96-7.90 (m, 3H), 7.77 (d, J=8.1 Hz, 1H), 7.58-7.48 (m, 3H), 7.42 (t, J=7.7 Hz, 1H), 7.14 (t, J=7.4 Hz, 1H), 7.08 (d, J=8.1 Hz, 1H), 3.88 (s, 3H)

13C-NMR(CDCL3)=δ 156.6, 136.2, 133.4, 132.4, 131.1, 130.6, 128.7, 128.1 (2C), 127.5, 127.1, 125.8, 125.7, 120.9, 111.2, 55.5.

Example 37

The same operation as in Example 1 was carried out except that 92 mg (0.60 mmol) of 2-methoxy-3-nitropyridine was used instead of 92 mg (0.60 mmol) of 4-nitroanisole and that 115 mg (0.90 mmol) of 3-thiopheneboronic acid was used instead of 110 mg (0.90 mmol) of phenylboronic acid, whereupon 54 mg (yield: 47%) of 2-methoxy-3-(thiophen-3-yl)pyridine as a white solid was obtained. The product was identified by 1H and 13C-NMR.

1H-NMR(CDCL3)=δ 8.12 (bd, J=4.7 Hz, 1H), 7.78 (bd, J=7.4 Hz, 1H), 7.75-7.71 (m, 1H), 7.47 (bd, J=4.7 Hz, 1H), 7.37 (dd, J=4.7, 3.4 Hz, 1H), 6.95 (dd, J=7.4, 4.7 Hz, 1H), 4.04 (s, 3H)

13C-NMR(CDCL3)=δ 160.5, 145.1, 137.0, 136.4, 127.7, 125.0, 123.8, 119.2, 117.0, 53.5.

Example 38

Into a 50 mL four-necked flask equipped with a thermometer and a condenser, a stirrer, 92 mg (0.60 mmol) of 4-nitroanisole, 110 mg (0.90 mmol) of phenylboronic acid, 9.1 mg (0.030 mmol) of palladium(II) acetylacetonate, 64 mg (0.12 mmol) of 2-dicyclohexylphosphino-3,6-dimethoxy-2',4',6'-triisopropylbiphenyl, 480 mg (1.8 mmol) of tripotassium phosphate n-hydrate, 16 mg (0.060 mmol) of 18-crown-6 and 3 mL of diethylene glycol dimethyl ether were added. The gas space of the four-necked flask was replaced with nitrogen, followed by stirring with heating under normal pressure at 130° C. for 24 hours. Then, the reaction liquid was cooled to room temperature. Methylene chloride was added to the reaction liquid, and the reaction liquid was subjected to filtration through celite. The filtrate was concentrated, and the obtained residue was dissolved in diethyl ether (20 mL) and mixed with a 30% aqueous hydrogen peroxide solution (5 mL). The solution was stirred at room temperature for 1 hour and then washed with distilled water (10 mL) and with a saturated aqueous iron(II) sulfate solution (10 mL). After extraction with diethyl ether (20 mL×3), the collected organic layer was washed with a saturated aqueous salt solution (10 mL). The organic layer was dried over anhydrous magnesium sulfate and concentrated, and the obtained residue was purified by medium pressure column chromatography (Biotage SNAP Ultra column (particle size: 25 μm), developing solvent: hexane/ethyl acetate) to obtain 53 mg (yield: 48%) of the desired 4-methoxybiphenyl as a white powder. The product was identified by 1H and 13C-NMR.

1H-NMR(CDCL3)=δ 7.59-7.51 (m, 4H), 7.42 (t, J=7.4 Hz, 2H), 7.31 (t, J=7.4 Hz, 1H), 6.99 (d, J=8.1 Hz, 2H), 3.86 (s, 3H).

13C-NMR(CDCL3)=δ 159.1, 140.8, 133.7, 128.7, 128.1, 126.7, 126.6, 114.2, 55.3.

Examples were summarized in the following Tables 1 to 3.

TABLE 1

| Example | Aromatic nitro compound | Boronic acid compound | Cross coupling reaction product | Isolation yield (%) |
|---|---|---|---|---|
| 1 | MeO—C6H4—NO2 | C6H5—B(OH)2 | MeO—C6H4—C6H5 | 76 |
| 2 | C6H5—C6H4—NO2 | C6H5—B(OH)2 | C6H5—C6H4—C6H5 | 65 |

TABLE 1-continued

| Example | Aromatic nitro compound | Boronic acid compound | Cross coupling reaction product | Isolation yield (%) |
|---|---|---|---|---|
| 3 | 4-F₃C-C₆H₄-NO₂ | C₆H₅-B(OH)₂ | 4-F₃C-C₆H₄-C₆H₅ | 55 |
| 4 | 3-O₂N-C₆H₄-CO₂Me | C₆H₅-B(OH)₂ | 3-(CO₂Me)-C₆H₄-C₆H₅ | 68 |
| 5 | 3,5-F₂-C₆H₃-NO₂ | C₆H₅-B(OH)₂ | 3,5-F₂-C₆H₃-C₆H₅ | 68 |
| 6 | 1-nitronaphthalene | C₆H₅-B(OH)₂ | 1-phenylnaphthalene | 82 |
| 7 | 2-nitronaphthalene | C₆H₅-B(OH)₂ | 2-phenylnaphthalene | 81 |
| 8 | 3-nitropyridine | C₆H₅-B(OH)₂ | 3-phenylpyridine | 79 |
| 9 | 4-MeO-C₆H₄-NO₂ | 4-Me-C₆H₄-B(OH)₂ | 4-MeO-C₆H₄-C₆H₄-4-Me | 79 |
| 10 | 4-MeO-C₆H₄-NO₂ | 4-F-C₆H₄-B(OH)₂ | 4-MeO-C₆H₄-C₆H₄-4-F | 73 |
| 11 | 4-morpholino-C₆H₄-NO₂ | C₆H₅-B(OH)₂ | 4-morpholino-C₆H₄-C₆H₅ | 63 |
| 12 | 4-Me-C₆H₄-NO₂ | 4-MeO-C₆H₄-B(OH)₂ | 4-MeO-C₆H₄-C₆H₄-4-Me | 78 |
| 13 | C₆H₅-NO₂ | 4-MeO-C₆H₄-B(OH)₂ | 4-MeO-C₆H₄-C₆H₅ | 72 |

TABLE 2

| Example | Aromatic nitro compound | Boronic acid compound | Cross coupling reaction product | Isolation yield (%) |
|---|---|---|---|---|
| 14 | 2-(4-nitrophenyl)-1,3-dioxolane | 4-MeO-C₆H₄-B(OH)₂ | 4'-methoxy-[1,1'-biphenyl]-4-carbaldehyde | 61 |
| 15 | 2-methyl-2-(4-nitrophenyl)-1,3-dioxolane | Ph-B(OH)₂ | 1-([1,1'-biphenyl]-4-yl)ethan-1-one | 72 |
| 16 | 4-nitro-(trifluoromethyl)benzene | 4-MeO-C₆H₄-B(OH)₂ | 4-methoxy-4'-(trifluoromethyl)-1,1'-biphenyl | 54 |
| 17 | 1-fluoro-4-nitrobenzene | 4-MeO-C₆H₄-B(OH)₂ | 4-fluoro-4'-methoxy-1,1'-biphenyl | 46 |
| 18 | 1-methoxy-3-nitrobenzene | Ph-B(OH)₂ | 3-methoxy-1,1'-biphenyl | 74 |
| 19 | 1,3-dimethyl-5-nitrobenzene | 4-MeO-C₆H₄-B(OH)₂ | 3,5-dimethyl-4'-methoxy-1,1'-biphenyl | 71 |
| 20 | 1-(methylsulfonyl)-3-nitrobenzene | Ph-B(OH)₂ | 3-(methylsulfonyl)-1,1'-biphenyl | 65 |
| 21 | 1-methyl-2-nitrobenzene | 4-MeO-C₆H₄-B(OH)₂ | 2-methyl-4'-methoxy-1,1'-biphenyl | 68 |
| 22 | 1-methoxy-2-nitrobenzene | Ph-B(OH)₂ | 2-methoxy-1,1'-biphenyl | 84 |
| 23 | 9-nitroanthracene | Ph-B(OH)₂ | 9-phenylanthracene | 44 |
| 24 | 2-methoxy-3-nitropyridine | Ph-B(OH)₂ | 2-methoxy-3-phenylpyridine | 80 |

TABLE 2-continued
| Example | Aromatic nitro compound | Boronic acid compound | Cross coupling reaction product | Isolation yield (%) |
|---|---|---|---|---|
| 25 | 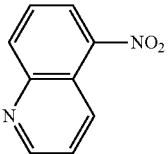 [SMILES: O=[N+]([O-])c1cccc2ncccc12] | 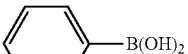 | 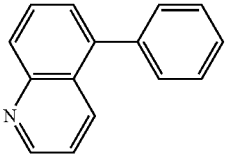 [SMILES: c1ccc(-c2cccc3ncccc23)cc1] | 71 |
| 26 | 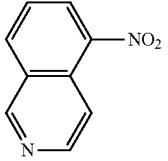 [SMILES: O=[N+]([O-])c1cccc2cnccc12] | 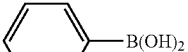 | 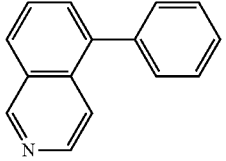 [SMILES: c1ccc(-c2cccc3cnccc23)cc1] | 70 |
TABLE 3
| Example | Aromatic nitro compound | Boronic acid compound | Cross coupling reaction product | Isolation yield (%) |
|---|---|---|---|---|
| 27 | 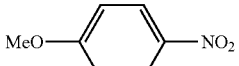 | 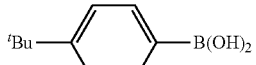 | 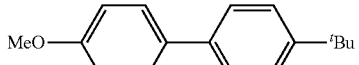 | 80 |
| 28 | 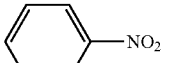 | 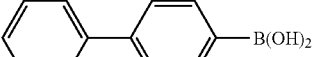 |  | 66 |
| 29 | 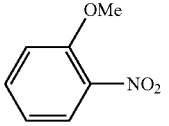 |  | 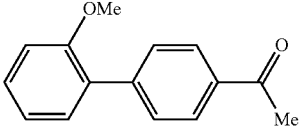 | 57 |
| 30 | 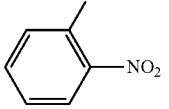 | 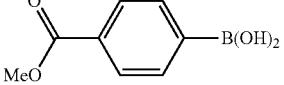 | 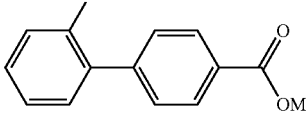 | 66 |
| 31 | 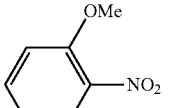 | 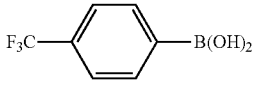 [SMILES: CC(C)(C)c1ccc(B(O)O)cc1] | 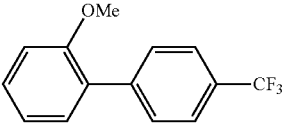 [SMILES: COc1ccccc1-c1ccc(C(F)(F)F)cc1] | 65 |
| 32 | 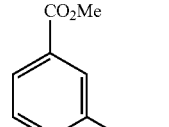 | 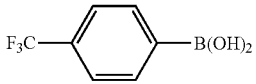 | 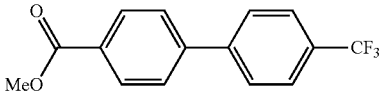 [SMILES: COC(=O)c1ccc(-c2ccc(C(F)(F)F)cc2)cc1] | 63 |
| 33 | 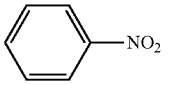 | 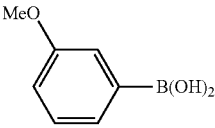 | 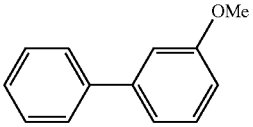 [SMILES: COc1cccc(-c2ccccc2)c1] | 72 |

TABLE 3-continued

| Example | Aromatic nitro compound | Boronic acid compound | Cross coupling reaction product | Isolation yield (%) |
|---|---|---|---|---|
| 34 | 2-nitroanisole | 2-methylphenylboronic acid | 2'-methyl-2-methoxybiphenyl | 67 |
| 35 | 1-nitronaphthalene | 2,6-dimethylphenylboronic acid | 1-(2,6-dimethylphenyl)naphthalene | 36 |
| 36 | 2-nitroanisole | 2-naphthylboronic acid | 2-(2-methoxyphenyl)naphthalene | 81 |
| 37 | 2-methoxy-3-nitropyridine | 3-thienylboronic acid | 2-methoxy-3-(3-thienyl)pyridine | 47 |
| 38 | 4-nitroanisole | phenylboronic acid | 4-methoxybiphenyl | 48 |

The entire disclosure of Japanese Patent Application No. 2016-213752 filed on Oct. 31, 2016 including specification, claims, drawings and summary is incorporated herein by reference in its entirety.

The invention claimed is:

1. A method for producing an aromatic compound represented by the following formula (3):

wherein $Ar^1$, $Ar^2$ and n are the same as defined in formulae (1) and (2),
which comprises subjecting an aromatic nitro compound represented by the following formula (1):

wherein $Ar^1$ is an aromatic hydrocarbon group which may have a substituent or a heteroaromatic group which may have a substituent, and n is an integer of from 1 to 5;
and a boronic acid compound represented by the following formula (2):

wherein $Ar^2$ is an aromatic hydrocarbon group which may have a substituent, or a heteroaromatic group which may have a substituent, $R^1$ is each independently a hydrogen atom, a $C_{1-4}$ alkyl group or a phenyl group, and the two $R^1$ substituents may be linked to form a ring containing oxygen atoms and a boron atom;
to a cross coupling reaction in the presence of a palladium or nickel compound as a transition metal catalyst.

2. The production method according to claim 1, wherein a phosphine compound coexists.

3. The production method according to claim 1, wherein the transition metal catalyst comprises a phosphine ligand represented by the following formula (4):

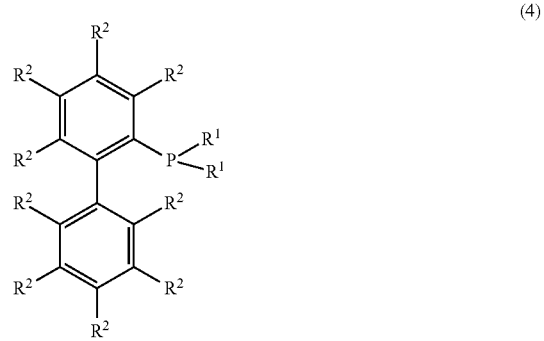

wherein $R^1$ is each independently a cyclohexyl group or a tert-butyl group and $R^2$ is each independently a hydrogen atom, a methyl group, a methoxy group, an isopropyl group, an isopropoxy group, a dimethylamino group, or a sulfonic acid group.

* * * * *